(12) United States Patent
Mao et al.

(10) Patent No.: US 6,379,693 B1
(45) Date of Patent: Apr. 30, 2002

(54) TRIVALENT CHROMIUM COMPLEX COMPOUND AND MILK PRODUCT CONTAINING THE SAME

(75) Inventors: Frank Chia Hung Mao, Taichung; Ling-Hui Cheng Chiang, Taipei, both of (TW)

(73) Assignee: Ling-Jui Cheng Chiang, Taipei (TW)

( * ) Notice: Subject to any disclaimer, the term of this patent is extended or adjusted under 35 U.S.C. 154(b) by 0 days.

(21) Appl. No.: 09/631,307

(22) Filed: Aug. 2, 2000

(51) Int. Cl.⁷ .............................................. A61K 47/00
(52) U.S. Cl. ........................ 424/439; 424/400; 426/74; 426/262; 426/656; 426/657
(58) Field of Search .................... 426/74, 262, 656; 424/439; 514/866, 870, 936

(56) References Cited

U.S. PATENT DOCUMENTS

| | | | |
|---|---|---|---|
| 3,234,001 A | | 2/1966 | Gaiser |
| 5,360,618 A | * | 11/1994 | Walker .......................... 426/72 |
| 5,681,600 A | * | 10/1997 | Antinone et al. ............... 426/4 |
| 5,985,339 A | * | 11/1999 | Kamarei ........................ 426/72 |
| 6,030,650 A | * | 2/2000 | Kamarei ........................ 424/72 |

OTHER PUBLICATIONS

Milchwissenschaft, 1990, 45(4), pp. 225–229, "Effect of heating and frozen storage . . . ", Maheshwari et al., see p. 225 re "Introduction" and "Materials & methods".

Inorganica Chim. Acta 1979, 33(2), pp. 149–153 "the chromium, manganese, cobalt . . . ", Ainscough et al., see p. 149.

Adv. Exp. Med. & Biol., 1974, 48, pp. 141–160, "Lactoferrin conformation . . . ", Parry et al., see p. 146 11.22–25.

* cited by examiner

Primary Examiner—James M. Spear
Assistant Examiner—Charesse L. Evans
(74) Attorney, Agent, or Firm—Bacon & Thomas

(57) ABSTRACT

The present invention is related to a method of producing a trivalent chromium complex compound by heating a trivalent chromium compound and lactoferrin together. The trivalent chromium complex compound can be added into milk to obtain trivalent chromium milk products. Both the complex compound and the milk products of the present invention can be served to diabetics for effectively reducing the concentration of blood sugar.

20 Claims, No Drawings

TRIVALENT CHROMIUM COMPLEX COMPOUND AND MILK PRODUCT CONTAINING THE SAME

BACKGROUND OF THE INVENTION

1. Field of the Invention

The present invention relates to a trivalent chromium complex compound and milk products containing the same, and a method of producing the complex compound and the milk products.

2. Description of Related Art

Generally, diabetic patients can be classified as having either type I or type II diabetes (non-insulin dependent diabetes mellitus, NIDDM). However about 90% of the diabetic patients have type II diabetes. In 1996, the World Health Organization and the International Diabetes Federation estimated that there are a total of 132 million diabetic patients worldwide and it will increase to 240 million in 2010. Approximately 3%–15% of the populations in many countries are affected by diabetes. Developing countries, such as China, will register the greatest increase in their diabetic population. Diabetes is a serious disease that we need to cure.

Trivalent chromium is found distributed in many tissues in our body, with the liver and kidney containing the highest amounts. It is a trace element that is needed to for the metabolism of sugar, protein and fat in the human body.

According to the study conducted in the United Kindom by Davies et al. (Metabolism, 46:469–473,1997) on 40,872 patients, it was observed that the chromium concentration in our serum decreases as we age. The serum chromium concentration is 0.5 ng/ml in babies and starts to decline until 0.3 ng/ml in adults over 70 years old. The concentration of chromium in sera of patients with type II diabetes, were usually 0.2 ng/ml, which is much below of the normal person which average around 0.5 ng/ml.

In addition, strenuous labor, pregnancy, obesity, old age, alcohol abuse, surgery and infection can all cause the excretion of trivalent chromium and lead to its deficiency. If not enough chromium is being replenished, the body will be deficient in this trace element, and cause the clinical symptoms of type II diabetes.

According to various researches, organic chromium may profitably improve insulin function, normal glucose metabolism, protein generation, lipid metabolism, plus reduce the possibility of maturity-onset diabetes and heart disease, and help in weight control.

The appropriate organic chromium, for example, chromium picolinate, chromium nicotinate, chromium GTF, chromium yeast extract, low-molecular weight Cr-binding substance, etc. , can be supplemented to diabetics for curing, or added into dietary supplements for adult.

U.S. Pat. No. 4,923,855 mentions a chromium-nicotinate GTF (glucose tolerance factor) material obtained by reacting an alkali metal salt of nicotinic acid with a trivalent chromium salt. U.S. Pat. No. 5,872,102 describes a method for a low-molecular weight Cr-binding substance isolated from bivine liver.

The present invention discloses another novel organic chromium complex compound and application thereof, and displays a method of producing the same.

SUMMARY OF THE INVENTION

The object of the present invention is to provide a trivalent chromium complex compound and milk products containing the same, which can be used to control diabetes.

It is another object of the present invention to provide a method for producing trivalent chromium complex compound and milk products containing the same.

To achieve the object, the procedure is performed primarily by heating a trivalent chromium compound and lactoferrin together to obtain the trivalent chromium complex compound, which can be further added into milk to obtain trivalent chromium milk products.

The milk used in the present invention is not strictly limited, e.g. milk of human, cow, goat, sheep, horse, deer, camel, etc. , preserved milk, concentrated milk, cheese, or milk powder.

The whey protein used in the present invention can be any unpurified whey protein obtained from cow milk, sheep milk, goat milk, human milk or milk of other mammals.

The lactoferrin used in the present invention can be cow lactoferrin, sheep lactoferrin, goat lactoferrin, human lactoferrin or lactoferrin from other mammals. Lactoferrin is a single-chained glycoprotein able to combine with metal ions, such as Fe(III), V(III), Cr(III), Mn(III), Co(III), etc., even in an acidic environment (pH=2 to 3). Each lactoferrin molecule can be bound with two Fe(III), and the binding positions are the same for both Cr(III) and Fe(III).

The lactoferrin primarily exists in whey, but it can also be found in tear, saliva, pancreatic juice, vagina secretion, sperm, etc. The lactoferrin is widely antibiotic, and able to regulate the immune system of human body.

By adding the trivalent chromium complex compound into milk, the trivalent chromium milk product is obtained, which can be effectively absorbed and utilized by the human body to supplement the organic chromium and hence effectively control the concentration of blood sugar.

The trivalent chromium complex compound and the milk products containing the same of the present invention can improve the normal metabolism of carbohydrates, therefore, it can be a healthy food or a therapeutic agent to relieve the symptoms of diabetics.

DETAILED DESCRIPTION OF THE PREFERRED EMBODIMENT

In the present invention, the method of producing the trivalent chromium complex compound includes the steps of: (a) providing at least a trivalent chromium compound, which can be selected from the group consisting of chromium (III) chloride with six molecules of crystal water, chromium (III) chloride, chromium (III) acetate, chromium (III) nitrate, chromium (III) oxide, chromium (III) sulfate, and other organic or inorganic trivalent chromium; (b) adding lactoferrin or whey protein to form a mixture; and (c) heating the mixture to obtain the trivalent chromium complex compound at a temperature range between 37° C. and 95° C. with stirring.

The method of producing the trivalent chromium milk products in the present invention includes the above procedure and a further step of: (d) adding the trivalent chromium complex compound into milk to obtain the trivalent chromium milk products.

In the present invention, the trivalent chromium compound can be selected from organic or inorganic chromium, e.g. chromium (III) chloride with six molecules of crystal water, chromium (III) chloride, chromium (III) acetate, chromium (III) nitrate, chromium (III) oxide, chromium (III) sulfate and other organic or inorganic trivalent chromium.

The heating temperature in the producing process ranges between 37° C. and 95° C., preferably between 60° C. and 80° C., and with full stirring for mixing well.

The lactoferrin used in the present invention can be cow lactoferrin, sheep lactoferrin, goat lactoferrin, human lactoferrin or lactoferrin from other mammals. Since the lactoferrin primarily exists in whey, the unpurified whey protein from various mammals can be used in the present invention.

To easily understand the present invention, please refer to the following examples which are used to describe the present invention, but not to limit the scope thereof.

EXAMPLE 1 lactoferrin (50 g) and chromium (III) chloride with six molecules of crystal water (5.125 g) are added to pure water (500 ml) and heated to around 72° C., stirring for 2 hours. Then the solution is cooled down to room temperature and filtered to eliminate impurity and obtain an organic chromium solution, which is then spray dried to obtain powdered trivalent chromium complex compound of the present invention.

EXAMPLE 2 lactoferrin (30 g), whey protein (200 g) and chromium (III) chloride with six molecules of crystal water (5.125 g) are added to pure water (1000 ml) and heated to around 70° C., stirring for 2 hours. Then the solution is cooled down to room temperature and filtered to eliminate impurity and obtain an organic chromium solution, which is then spray dried to obtain powdered trivalent chromium complex compound of the present invention.

EXAMPLE 3

Repeat steps of Example 1, but the organic chromium solution is mixed with 100 kg milk powder through spray drying, then the trivalent chromium milk product can be obtained.

EXAMPLE 4

Repeat steps of Example 2, but the organic chromium solution is mixed with 100 kg milk powder through spray drying, then the trivalent chromium milk product can be obtained.

EXAMPLE 5

Repeat steps of Example 1, but the organic chromium solution is added into 900 kg fresh milk, then the fresh trivalent chromium milk product can be obtained.

TEST EXAMPLE I

The trivalent chromium milk product from Example 3 is added into rodent diet (Lab Diet, 5001 Rodent Diet, PMI Nutrition International, Inc., Missouri, U.S.A.) of the test group (400 ppb chromium III), but not added into that of the control group. Male mice (KK/H1J), 12-week old, having congenital type II diabetes, are fed with or without the trivalent chromium milk product for two weeks, and followed by a 12-hour fast. Then the mice of the test and control groups are fed with glucose (1 g glucose/kg body weight) by gavage for a glucose tolerance test, in which the blood sugar (mg/dl) of the test group is compared with that of the control group, i.e., mice fed without the trivalent chromium milk product, after 0,2, and 4 hours. The results are listed in Table 1.

TABLE 1

Glucose tolerance test for mice (KK/H1J) having congenital type II diabetes fed with or without trivalent chromium milk product for two weeks

| | blood sugar after 0 hour (mg/dl) | blood sugar after 2 hours (mg/dl) | blood sugar after 4 hours (mg/dl) |
|---|---|---|---|
| Test group[a] | 95 ± 8 | 208 ± 9** | 124 ± 8 |
| Control group[b] | 95 ± 8 | 263 ± 14** | 144 ± 9 |

[a]for 10 mice;
[b]for 8 mice;
**for $P < 0.01$

As shown in the table 1, the blood sugar of mice fed with the trivalent chromium milk product is significantly lower than that of mice fed a diet without trivalent chromium after 2 hours ($P<0.01$).

TEST EXAMPLE 2

The trivalent chromium milk product from Example 3 is added into rodent diet (Lab Diet, 5001 Rodent Diet, PMI Nutrition International, Inc., Missouri, U.S.A.) of the test group (200 ppb chromium III), but not added into that of the control group. Female mice (C57BLKS/J-lepr$^{db}$), 7-week old, having congenital obesity type II diabetes, are fed with or without trivalent chromium milk product for four months. Then the non-fasting blood sugar (mg/dl) of the test as well as control groups is tested. The results are shown on Table 2.

TABLE 2

Test results of mice (C57BLKS/J-lepr$^{db}$) with inborn obesity type II diabetes fed with or without trivalent chromium milk product for four months

| | blood sugar before test (mg/dl) | blood sugar after test (mg/dl) |
|---|---|---|
| Test group[a] | 489 ± 8 | 434 ± 18* |
| Control group[b] | 470 ± 8 | 514 ± 20* |

[a]for 5 mice;
[b]for 5 mice;
*for $P < 0.05$

As shown in the table 2, the blood sugar of mice fed with trivalent chromium milk product is significantly lower than that of mice fed a diet without trivalent chromium ($P<0.05$).

TEST EXAMPLE 3

The trivalent chromium milk product from Example 4 is added into rodent diet (Lab Diet, 5001 Rodent Diet, PMI Nutrition International, Inc., Missouri, U.S.A.) of the test group (400 ppb chromium III), but not added into that of the control group. Male ICR mice, 8-week old, having type I diabetes induced by STZ (streptozotocin), are fed with or without trivalent chromium milk product for four weeks. Then the non-fasting blood sugar (mg/dl) of the test as well as control groups is tested. The results are shown on Table 3.

TABLE 3

Test results of ICR mice with type I diabetes induced by STZ, fed
with or without trivalent chromium milk product for four weeks

|  | blood sugar before test (mg/dl) | blood sugar after test (mg/dl) |
|---|---|---|
| Test group[a] | 453 ± 24 | 364 ± 11* |
| Control group[b] | 454 ± 24 | 422 ± 21* |

[a]for 8 mice;
[b]for 8 mice;
*for P < 0.05

As shown in the table 3, the blood sugar of mice fed with trivalent chromium milk product is significantly lower than that of mice fed a diet without trivalent chromium (P<0.05).

Accordingly, the trivalent chromium milk products of the present invention can be a healthy food or a therapeutic agent to be served with diets of diabetics for effectively reducing blood sugar. In addition, the method of producing the complex compound and its milk products in the present invention is a simple and efficient process, which is profitably applied in manufacturing.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A method of producing a trivalent chromium complex for controlling diabetes, said method comprising steps of:
   (a) providing at least one of trivalent chromium compound which is selected from the group consisting of chromium (III) chloride with six molecules of crystal water, chromium (III) chloride, chromium (III) acetate, chromium (III) nitrate, chromium (III) oxide, chromium (III) sulfate and otherorganic/inorganictrivalent chromium compounds;
   (b) adding lactoferrin or whey protein to form a mixture; and
   (c) obtaining the trivalent chromium complex.

2. The method of claim 1, wherein the lactoferrin or whey protein is selected from the group consisting of cow lactoferrin, sheep lactoferrin, goat lactoferrin, human lactoferrin, unpurified cow whey protein, unpurified sheep whey protein, unpurified goat whey protein, and unpurified human whey protein.

3. The method of claim 1, wherein the trivalent chromium complex of the step (c) is obtained by heating the mixture of step (b), the heating temperature in the step (c) ranges between 37° C. and 95° C., and the mixture is mixed well by stirring.

4. The method of claim 1, wherein the trivalent chromium compounds are selected from the group consisting of chromium (III) chloride with six molecules of crystal water, chromium (III) chloride, chromium (III) acetate, chromium (III) nitrate, chromium (III) oxide, and chromium (III) sulfate.

5. A method of producing a trivalent chromium milk product for controlling diabetes, said method comprising steps of:
   (a) providing at least one of trivalent chromium compound which is selected from the group consisting of chromium (III) chloride with six molecules of crystal water, chromium (III) chloride, chromium (III) acetate, chromium (III) nitrate, chromium (III) oxide, chromium (III) sulfate, and other organic and inorganic trivalent chromium compounds;
   (b) adding lactoferrin or whey protein to form a mixture;
   (c) obtaining a trivalent chromium complex; and
   (d) adding the trivalent chromium complex into milk to obtain a trivalent chromium milk product, wherein the milk is selected from fresh milk, preserved milk, concentrated milk, cheese, and milk powder of various mammals.

6. The method of claim 5, wherein the lactoferrin or whey protein is selected from the group consisting of cow lactoferrin, sheep lactoferrin, goat lactoferrin, human lactoferrin, unpurified cow whey protein, unpurified sheep whey protein, unpurified goat whey protein, and unpurified human whey protein.

7. The method of claim 5, wherein the trivalent chromium complex of the step (c) is obtained by heating the mixture of step (b), the heating temperature in the step (c) ranges between 37° C. and 95° C., and the mixture is mixed well by fully stirring.

8. The method of claim 5, wherein the trivalent chromium compounds are selected from the group consisting of chromium (III) chloride with six molecules of crystal water, chromium (III) chloride, chromium (III) acetate, chromium (III) nitrate, chromium (III) oxide, and chromium (III) sulfate.

9. A trivalent chromium complex for controlling diabetes, which is produced by adding a trivalent chromium compound to lactoferrin or whey protein; wherein the trivalent chromium compound is selected from the group consisting of chromium (III) chloride with six molecules of crystal water, chromium (III) chloride, chromium (III) acetate, chromium (III) nitrate, chromium (III) oxide, and chromium (III) sulfate; and the lactoferrin or whey protein is selected from the group consisting of cow lactoferrin, sheep lactoferrin, goat lactoferrin, human lactoferrin, unpurified cow whey protein, unpurified sheep whey protein, unpurified goat whey protein, and unpurified human whey protein.

10. A trivalent chromium milk product for controlling diabetes, which is produced by adding the compound of claim 9 into milk, wherein the milk is selected from the group consisting of fresh milk, preserved milk, concentrated milk, cheese, and milk powder of various mammals.

11. A trivalent chromium complex for controlling diabetes, which is a complex of trivalent chromium compounds and lactoferrins.

12. The complex of claim 11, wherein said trivalent chromium compound is selected from the group consisting of chromium (III) chloride with six molecules of crystal water, chromium (III) chloride, chromium (III) acetate, chromium (III) nitrate, chromium (III) oxide, chromium (III) sulfate and other organic/inorganic trivalent chromium compounds.

13. The complex of claim 11, wherein said trivalent chromium compound is selected from the group consisting of chromium (III) chloride with six molecules of crystal water, chromium (III) chloride, chromium (III) acetate, chromium (III) nitrate, chromium (III) oxide, and chromium (III) sulfate.

14. The complex of claim 11, wherein said trivalent chromium compound is chromium (III) chloride with six molecules of crystal water.

15. The complex of claim 11, wherein said lactoferrin is selected from the group consisting of cow lactoferrin, sheep lactoferrin, goat lactoferrin, and human lactoferrin.

16. A method for controlling diabetics in a patient, said method comprising administering to said patient an effective amount of a trivalent chromium complex of trivalent chromium compounds and lactoferrins.

17. The method of claim 16, wherein said trivalent chromium compounds are selected from the group consisting of chromium (III) chloride with six molecules of crystal water, chromium (III) chloride, chromium (III) acetate, chromium (III) nitrate, chromium (III) oxide, chromium (III) sulfate orotherorganic/inorganictrivalent chromium compounds.

18. The method of claim 16, wherein said trivalent chromium compounds are selected from the group consisting of chromium (III) chloride with six molecules of crystal water, chromium (III) chloride, chromium (III) acetate, chromium (III) nitrate, chromium (III) oxide, or chromium (III) sulfate.

19. The complex of claim 16, wherein said trivalent chromium compounds are chromium (III) chloride with six molecules of crystal water.

20. The complex of claim 16, wherein said lactoferrins are selected from the group consisting of cow lactoferrin, sheep lactoferrin, goat lactoferrin, or human lactoferrin.

* * * * *

UNITED STATES PATENT AND TRADEMARK OFFICE
CERTIFICATE OF CORRECTION

PATENT NO. : 6,379,693 B1  Page 1 of 1
DATED : April 30, 2002
INVENTOR(S) : Mao et al.

It is certified that error appears in the above-identified patent and that said Letters Patent is hereby corrected as shown below:

<u>Title page,</u>
Item [73], please correct the Assignee name to read:
-- Ling-Hui Cheng Chiang, Taipei (TW) --

Signed and Sealed this

Twenty-fifth Day of February, 2003

JAMES E. ROGAN
*Director of the United States Patent and Trademark Office*